United States Patent [19]

Blesener

[11] Patent Number: 5,085,500
[45] Date of Patent: Feb. 4, 1992

[54] NON-IMAGING LASER PARTICLE COUNTER

[75] Inventor: James L. Blesener, White Bear Lake, Minn.

[73] Assignee: TSI Incorporated, St. Paul, Minn.

[21] Appl. No.: 442,546

[22] Filed: Nov. 28, 1989

[51] Int. Cl.$^5$ ...................... G01N 21/00; G01N 15/06
[52] U.S. Cl. ................................... 356/338; 356/340; 356/343; 250/574
[58] Field of Search ................ 356/338, 337, 339–343; 250/574, 573

[56] References Cited

U.S. PATENT DOCUMENTS

| | | |
|---|---|---|
| 2,682,613 | 6/1954 | Une . |
| 3,614,231 | 10/1971 | Shaw ..................................... 356/37 |
| 3,770,351 | 11/1973 | Wyatt ..................................... 356/102 |
| 3,835,315 | 9/1974 | Gravitt, Jr. ........................... 250/218 |
| 3,851,169 | 11/1974 | Faxvog ................................. 250/222 |
| 3,989,381 | 11/1976 | Fulwyler ............................... 356/39 |
| 4,178,103 | 12/1979 | Wallace ................................. 356/336 |
| 4,188,121 | 2/1980 | Hirleman, Jr. et al. ............. 356/336 |
| 4,189,236 | 2/1980 | Hogg et al. ........................... 356/317 |
| 4,783,599 | 11/1988 | Borden ................................. 356/341 |
| 4,804,853 | 2/1989 | Borden et al. ....................... 356/338 |
| 4,871,249 | 10/1989 | Watson ................................. 356/73 |

FOREIGN PATENT DOCUMENTS

| | | |
|---|---|---|
| 0257248 | 3/1988 | European Pat. Off. . |
| 61-35335 | 5/1986 | Japan . |
| 0154969 | 6/1987 | Japan . |
| 0177001 | 7/1987 | Japan . |
| 62-220833 | 11/1987 | Japan . |
| 0716654 | 10/1954 | United Kingdom . |

OTHER PUBLICATIONS

Review of Scientific Instrument, vol. 51, No. 8; Aug. 1980, pp. 1049–1058, K. Suda.
Benefits of Real Time, In Situ Particle Monitoring in Production Medium Current Implantation, Borden et al.
Diehl, Smith and Sydor, "Analysis of Suspended Solids by Single-Particle Scattering," *Applied Optics*, vol. 18, No. 10 (May 1979).
Schehl, Ergun and Headrick, "Size Spectrometry of Aerosols Using Light Scattering from the Cavity of a Gas Laser," *Review of Scientific Instruments*, vol. 44, No. 9 (Sep. 1973).
Marple, "The Aerodynamic Size Calibration of Optical Particle Counters by Inertial Impactors," *Aerosol Measurement* (1979).
Elterman, "Brewster Angle Light Trap," *Applied Optics*, vol. 16, No. 9 (Sep. 1977).
Jin, Sugimoto and Sate, "Development of a New Laser Particle Counter (A-18)".

Primary Examiner—Richard A. Rosenberger
Assistant Examiner—Hoa Pham
Attorney, Agent, or Firm—Merchant, Gould, Smith, Edell, Welter & Schmidt

[57] ABSTRACT

A non-imaging particle counter 10 utilizing one or more detectors 25 which directly collect light scattered by particles in a fluid traversing a sensing volume 63. The detectors 25, are non-imaging, non-focusing, optic-less light collection devices, such as large area photodiodes. The detectors 25 are arranged and configured proximate the sensing volume 63, but such that the beam of light 60 is not operatively incident thereon. The beam of light 60 is provided by a laser 50 and is shaped by a focusing/collimating lens 54. The beam of light 60 passes through several apertures 51–53 to reduce stray/background light in the system. The detectors 25 are oriented at an angle with respect to the plane formed by the longitudinal axis of the beam and the flow of fluid, wherein stray light 61 strikes the detectors 25 at an angle greater than the acceptance angle of the detectors 25, while scattered light strikes the detectors 25 at an angle less than the detectors' 25 acceptance angle. A light stop 31 having a Brewster angle for the wavelength of the beam of light 60 is utilized as a beam stop. Further, a coincidence detection circuit 100 provides for reducing spurious counts caused by ionizing emissions and/or other noise.

20 Claims, 5 Drawing Sheets

NON-IMAGING LASER PARTICLE COUNTER

FIELD OF THE INVENTION

This invention relates generally to the detection of particles, and more specifically to the detection of single particles using light scattering techniques and non-imaging detection of the scattered light.

BACKGROUND OF THE INVENTION

Fabrication techniques in the semiconductor industry currently utilize line widths below 1 micrometer (um) and layer thicknesses below 0.1 um. Due to these small dimensions, airborne contamination in the form of small particles can cause defects in semiconductor devices when the airborne contaminants come into contact with the semiconductor during the manufacturing process. Therefore, the environmental conditions under which semiconductor devices are manufactured are monitored closely to avoid such contamination. Typically, the semiconductor devices are manufactured in "clean room" type environments. To maintain the clean room status, the room is monitored to detect and control airborne contamination. Careful monitoring thereby aids the quality control of the semiconductor manufacturing process. As is well known in the art, there are multiple techniques for monitoring and sizing particles suspended in air, or more generally in a fluid. Optical detection of light scattered by the particles (hereafter referred to as "light scattering" for convenience) is often used.

Typically, a light scattering particle counter draws a sample of air through a beam of light. The particles in this sample flow of air scatter light in proportion to their size, shape and index of refraction. Refractive, reflective, or other light collection techniques are used to enhance the collection of light and focus it onto a photoelectric device. The photoelectric device converts the scattered light into an electrical signal. The created electrical signal is related to the amount of incident light and thus the particle size. Additionally, the signal is typically a pulse, wherein the signal width represents the velocity of the particle and the beam width. By accumulating the pulses over a period of time, the concentration of particles in the sample air flow may be determined.

The theoretical particle size limit for detecting particles by this method is approximately 0.05 um (particle diameter) (See e.g., Knollenberg and Luehr, 1976). However, those skilled in the art typically recognize the practical limit of this technique, at this time, to be 0.1 um.

One typical light scattering device is the Model 3755 LPC Laser Particle Counter manufactured by TSI, Inc., of St. Paul, Minn., the assignee of the present invention. This device utilizes a plurality of lenses to collect light scattered by contaminant particles in an air flow passing through a laser beam. The collected light is focused onto a single detector. The detector generates electrical signals in response to the incident light, with the signals being subsequently counted. Using this arrangement, the device is capable of measuring particles down to 0.5 um. However, as noted above, the trend toward smaller semiconductor fabrication techniques is continuing, therefore instruments capable of measuring smaller particles are required. There is also a trend to decrease the size of clean rooms. As the size of clean rooms' reduce to small work stations, the need for smaller, more compact and more reliable monitoring devices arises.

A further limitation of typical light scattering devices is the devices' sizing capabilities. This limitation is due to the devices' limited ability to collect the scattered light. As is well known, if a large percentage of the scattered light is detected, then a better indication of pulse intensity and thereby particle size is achieved. Optimally, all directional components (i.e., forward, backward and side) of the scattered light should be collected. By increasing the total collected light, the signal to noise ratio of a device may be improved.

Another drawback of many of these light scattering devices is that they use expensive optics to gather the scattered light. Also, these devices may indicate the presence of particles when none are present due to their limited finite electrical noise immunity, as well as by measuring ionizing radiation incident on the devices' detector(s).

Therefore, there arises a need for a light scattering device which is smaller and remedies the above described drawbacks.

SUMMARY OF THE INVENTION

The present invention provides for an improved method and apparatus for determining the concentration and size of fluid borne particles by means of a light scattering device (hereinafter referred to as the "counter" for convenience), while simultaneously eliminating size and cost constraints inherent in the above mentioned typical light scattering devices. The present invention provides for reducing the size of the system and utilizing a non-imaging, non-focusing optic-less light collection/detection means. The present invention works extremely well for the purpose of detecting (and/or monitoring) and sizing particles in a fluid sample. However, the invention is not so limited and is to be included within the broad scope of the appended claims.

Preferably, a device constructed according to the principles of the present invention includes a light source, which generates a beam of light. The beam intersects with a fluid source which may contain particles. The intersection of the beam and the fluid source defines a sensing volume. The sensing volume is directly monitored by detection means, preferably large area photodiodes, thereby eliminating the need for optical reimaging techniques to collect the light scattered by particles in the sensing volume. In this manner, the present invention eliminates the need for expensive lenses, while collecting a greater amount of the scattered light. In addition, the present invention eliminates the losses associated with the lenses, as described further below. Therefore, the invention improves signal-to-noise because of the greater light intensity monitored and thereby increases particle sizing capability.

In a preferred embodiment apparatus, the counter continuously draws a sample of fluid through a laser beam by way of vacuum means during operation. Particles contained in the fluid scatter light as they pass through the beam. As previously noted, the light which is scattered from the particle is related to the particle's size, shape, and index of refraction. This scattered light is then converted to an electrical signal by photoelectric devices. These devices respond to the incident scattered light directly so as to eliminate transmittance losses due to reimaging optics.

Additionally, the present invention uses several other features. One feature provides for background light from the laser to reflect from the detector means, while the scattered light is absorbed to produce the photo electric signal. This feature is preferably implemented by, first, ensuring that the angle of incidence of the background light is greater than the critical acceptance angle of the detector means. As those skilled in the art will recognize, an "acceptance angle" is that angle, relative to the normal to the object, at which light striking the object at an angle greater than the acceptance angle is absorbed. As used herein, the angle is measured relative to the normal such that light reflects off of the object if the angle of incidence is greater than the acceptance angle.

Second, the angle of incidence on the detectors of the scattered light from particle(s) intersecting the sensing volume must be within, or less than, the detector means+ critical acceptance angle. By arranging and configuring the detector means to satisfy these two conditions, a nonimaging particle counter with a low background light level is achieved. Additionally, since the noise level of the detector is proportional to the background light level incident upon the detector, a better signal-to-noise ratio is achieved.

Another feature of a preferred embodiment is the counter's utilization of coincidence detection means. In the preferred embodiment, the coincidence detection means is implemented through a coincidence detection circuit. This circuit requires the use of two or more detector means and allows the counter to eliminate spurious counts by requiring each detector to simultaneously detect incident light. As those skilled in the art will recognize, the scattering of light from the particles intersecting the sensing volume is symmetrical. Therefore, by orienting and configuring two or more detector means and by requiring coincident signals, spurious particle counts created by electronic noise or ionizing emissions are eliminated due to the low probability of the detectors encountering such signals at the same time.

Therefore, according to one aspect of the invention, there is provided a continuous flow particle counter apparatus, of the type wherein a sample fluid is passed through a beam of light, wherein the intersection of the sample fluid and beam of light define a sensing volume, and wherein particles suspended in the sample fluid scatter light, the particle counter comprising:

Sensor means for directly collecting the scattered light and generating signals responsive to the scattered light, whereby reimaging optics are not required.

According to a further aspect of the invention, there is provided an apparatus as recited above wherein said sensor means are arranged and configured to reflect stray light from the vicinity of the light source and absorb the scattered light.

According to another aspect of the invention, there is provided a particle counter apparatus, of the type wherein particles suspended in a sample fluid flow scatter light, the apparatus comprising:
 (a) a source of light;
 (b) a lens, said lens arranged and configured to shape light from said source into a beam, said beam intersecting the fluid flow forming a sensing volume; and
 (c) one or more large area photodetectors arranged and configured such that said beam operatively passes said photodetector without being operatively incident, said photodetector including a light sensitive surface generally defining a mean plane, said photodetector oriented wherein said mean plane is located proximate the sensing volume, whereby said photodetector directly collects the scattered light without requiring reimaging optics in order to detect particles in the sample fluid.

These and other advantages and features which characterize the invention are pointed out with particularity in the claims annexed hereto and forming a part hereof. However, for a better understanding of the invention, its advantages and objectives obtained by its use, reference should be had to the Drawing which forms a further part hereof and to the accompanying descriptive matter, in which there is illustrated and described a preferred embodiment of the invention.

While the invention will be described with respect to a preferred embodiment configuration and with respect to particular components therein, it will be understood that the invention is not to be construed as limited in any manner by either such configuration or components.

BRIEF DESCRIPTION OF THE DRAWING

Referring to the Drawing, wherein like numbers represent like parts throughout the several views:

FIG. 4b is an enlarged view of a portion of FIG. 4a;

DETAILED DESCRIPTION OF THE INVENTION

As mentioned above, the principles of this invention apply particularly well to its application as a particle counting light scattering device. This invention provides for an accurate determination of particle size, velocity (or flow, wherein flow equals velocity, interpolated by the beam cross sectional area and the time that the particle was in the beam, times the inlet flow area) and concentration in a given fluid sample by using light scattering and direct non-imaging light collection techniques. The invention also uses coincidence detection circuitry to avoid including spurious counts due to noise sources. The preferred embodiment, described below, is compact in design and its many elements interact with each other to make an efficient, reliable measurement instrument.

To more fully understand the present invention, a description of the preferred embodiment will be deferred pending a brief discussion of the light scattering and non-imaging light collection principles and techniques utilized by the present invention.

As is well known, light may undergo multiple interactions when it encounters a particle. The five major interactions of particles and light are as follows: (1) diffraction, when photons of light pass by the particle and are bent toward or away from it; (2) refraction, when photons pass through the particle and their path is changed because of the different indices of refraction of the two media; (3) reflection, when photons hit the particle and are reflected away; (4) absorption, when photons hit the particle and are absorbed into it, transforming their energy into heat; and (5) thermal emission, when particles cool and emit photons. See, for example, Bohren and Huffman, *Absorption and Scattering of Light by Small Particles* (1983), for a more thorough discussion of such light interactions.

Diffraction, refraction and reflection may be collectively described as "scattered" light. The principles of light scattering are well known to those skilled in the art and so will herein be discussed in a cursory fashion. However, for a more detailed discussion, reference may be had to H. C. van de Hulst, *Light Scattering by Small Particles* (1981).

Scattered light, C(sca) may be represented by the following equation:

$$C(sca) = 1/k^2 \int f(\theta,\phi) d\omega.$$

Where k is $2^*\pi/\lambda$, a constant to adjust for wavelength dependencies; $d\omega = \sin(\theta) d\theta d\phi$; and $\lambda$ is the wavelength of light. From the foregoing, one can easily see that the scattering integral is calculated over some $d(\theta)$ and $d(\phi)$ angular range. As $d(\theta)$ and $d(\phi)$ approach 360 degrees, it can be shown that the light scattered into the $d(\theta)$ $d(\phi)$ angular region approaches 100% of the total light scattered.

In the present invention, an x-y-z coordinate system will be used to describe the invention rather than polar coordinates ($\theta$ and $\phi$) for the purposes of ease of description and understanding of the present invention. In the present invention, the $d(\theta)$ and $d(\phi)$ are the angular representations of the detector position with respect to the axis of the beam. In the x-y-z Cartesian coordinate system, the origin may be located at the point at which the fluid source flow intersects the beam. Therefore, the x-y-z coordinate system may be further defined as follows: the longitudinal axis of the beam defines the x-axis, the longitudinal axis of the fluid source flow through the beam defines the z-axis and the normal to the plane formed by the x and z axes defines the y axis.

Light scattering may be considered in two ranges of approximation for the counter's 10 intended use dependent upon the relationship between the wavelength of light and the particle diameter. The first range of approximation is known as Rayleigh scattering. This range is appropriate when the wavelength of light is much greater than the diameter of the particles to be measured. As those skilled in the art will recognize, the particle to be measured is that particle on which the light is incident. In this range of light scattering, the main interactions of the light wave with the particle are diffraction, refraction, reflection, absorption and emission.

The second range of approximation is called geometric scattering. This range applies when the diameter of the particle is much greater than the wavelength of the light source.

Alternatively, Mie scattering theory may be used to provide an exact solution to the light scattering phenomenon over the entire range of particle sizes versus wavelength spectrum. However, due to the Mie theory calculation technique's complexity in the geometric scattering regions, Mie scattering theory is usually used only when the wavelength of light is approximately equal to or greater than the particle diameter.

As is well known to those skilled in the art, any combination of the foregoing light phenomena may be used for particle sensing predictions.

As discussed above, size constraints are pertinent to these types of devices. In order to reduce size, the preferred embodiment light scattering counter 10 (seen in FIG. 1-6 described below) was designed to maximize efficiency while minimizing the counter's 10 "footprint" and volume. The larger components of typical optical light scattering designs are the collection optics. The present invention, however, does not use collection optics to collect the light and focus it onto detectors 25. Instead, the detectors 25 directly absorb the scattered light. As an advantage of such a design, a more efficient system results (i.e., there are no transmission losses associated with collection optics and/or lenses). The detectors 25 therefore "see" a greater amount of light and thus produce a larger signal to noise ratio (i.e., since there are no transmission losses, a greater portion of the scattered light falls on or is incident on the detectors 25). Also, since there are no lenses, the counter 10 is much smaller than other typical current devices. Still further, with the new designs of solid state photodiodes and the symmetrical scattering of light, the detector's 10 ability to collect the scattered light provides for a larger solid angle of collecting than most designs.

A second design consideration of the counter 10 is the arrangement and configuration of the laser beam so as to keep stray light within the detection chamber 26 (described below) to a minimum.

Previously, apertures were used along the beam emitted from the laser, but this approach requires a system of significant length. To avoid this drawback, the major contributing source of stray light in such devices was attacked. Many typical laser diodes emit light from both a front facet and a back facet, or first and second facets respectively (not shown). The back facet is used to enable monitoring of the laser power from an internally placed photo diode (not shown), as well as emit light in the "backward" direction. The light emitted from the back facet is both absorbed on an internal photodiode and reflected from it. The light reflected from it is often allowed to re-enter the system and is considered stray light since it is not entering the system at the same angle as the light out of the front laser facet into the collimating or focusing lens. If the exact angles of light acceptance from the front facet of the laser to the collimating lenses are calculated, an aperture can be designed to block most of the stray light (i.e., light not from the laser front facet and within the collimating lens' acceptance angle(s)) and still allow virtually all of the desired light through the aperture. If the stray light enters the detection chamber 36 through the collimating lens 54 it would be considered background light 61 due to its directional components with respect to the longitudinal axis of the laser beam 60. The key design consideration is that the aperture is placed directly on (or proximate to) the laser diode case and is designed for the specific collimating lens and laser used. This effectively reduces the amount of light emitted from the back facet of the diode laser that is scattered into the detector chamber 36 (described below) and thereby reduces the light which reaches the system photodetectors and is monitored as background light. This allows for a much more compact design with much better results (i.e., better signal-to-noise among others).

A third feature of the present invention is the reduction of stray light which strikes the detectors' within the detectors' acceptance angle. The small size of the overall system relative to the laser beam dimensions and the diffraction limits of the optics makes it virtually impossible to prevent all background light from striking the detectors 25. However, a key feature of the design takes advantage of the fact that the background light has a different incident angle onto the detectors 25 than the incident angle of light scattered by particles. The differing angles of incidence are due to the light origins and the detector 25 positions. Therefore, the detectors 25 are placed at an angle with respect to the x-z plane formed by the sample fluid flow and laser beam so as to be reflective to the background light and absorptive to the light arriving from angles where particles are to be detected. This provides a significant signal/noise improvement while preserving the compact size of the counter 10.

The signal to noise level is increased when the stray light is decreased because the stray light adds an average dc current in the detectors 25. This noise level of the detectors 25 is proportional to the current in the individual detectors 25. By eliminating this incident light on the detectors 25 and still allowing the scattered light to be absorbed by the detectors 25, the counter's 10 functionality is optimized. Those skilled in the art will recognize that by reducing the incident light into the detector, the current through the detector is reduced, and the current shot noise in the detector is thereby reduced.

As one skilled in the art will realize, if any incident nonscattered light reaching the detectors 25 has any power fluctuations on it, then these fluctions will increase the system noise and thereby reduce its particle detection sensitivity. Since the only light source in the counter 10 is the illuminating lasers, one can monitor its power output and monitor power changes directly. These power changes can then be subtracted from the signal out of the detectors 25. For example, if the laser increases in intensity, the corresponding change in the signal from the detectors 25 is merely subtracted. This allows for a system that is less susceptible to laser power fluctuations.

Figure 1:
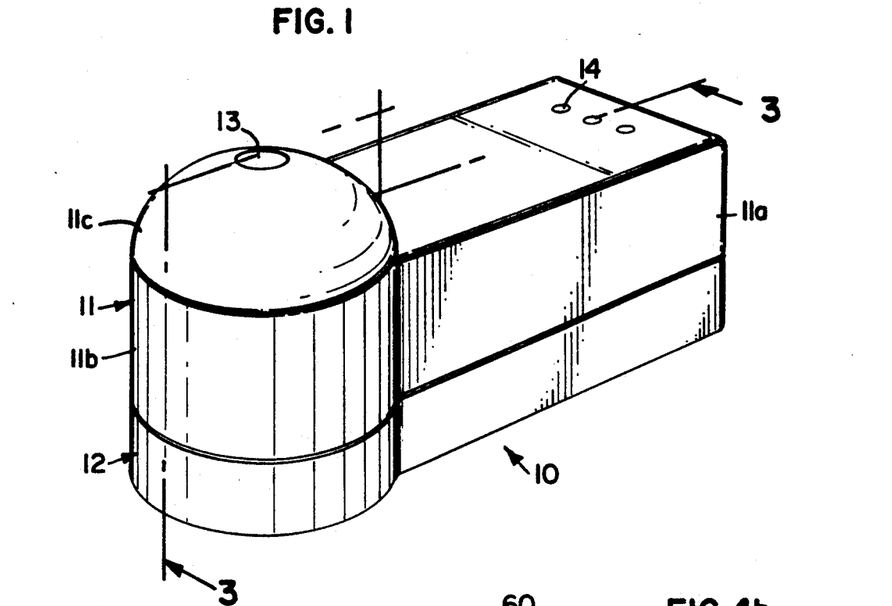
FIG. 1 is a perspective drawing of a counter 10 constructed according to the principles of the present invention.
Figure 4A:
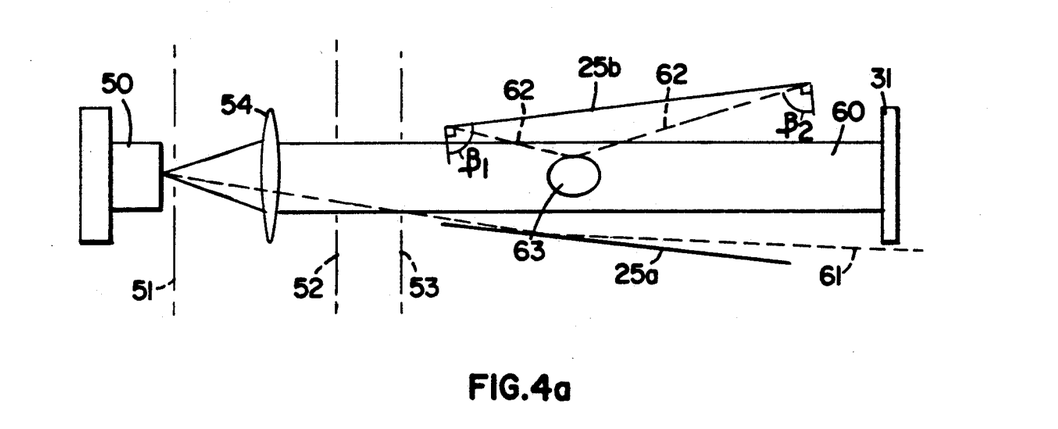
FIG. 4a is a diagrammatic view of the arrangement and geometry of the detectors 25a, 25b with respect to the beam 60, sensing volume 63, laser 50 and light blocking members 51, 52 and 53 of the counter 10 of FIG. 1.

Turning now to a discussion of a preferred embodiment, an example of a preferred light scattering counter constructed according to the principles of the present invention is illustrated in FIG. 1. An unscaled illustration of the detection elements and sensing volume contained in the detection chamber housing 20 is illustrated in FIG. 4. The light scattering counter is illustrated generally at 10 in FIG. 1.

Referring first to FIG. 1, in general the counter 10 is rectangular with a "silo-shaped" portion attached to one end. The rectangular counter 10 has a top cover 11 and base 12 which come together in a rabbet-type joint fashion (best seen in FIG. 2). Top cover 11 is a single piece comprised of first portion 11a, second portion 11b and third portion 11c.

The counter 10 has an inlet 13 and exit 16 (best seen in FIG. 2) to provide for the fluid sample to be drawn through the counter 10. Vacuum means, described below, may be located either internal or external to the counter 10. Three LED's 14 are provided so as to provide an indication of fluid flow, particle detection, and on/off status. Outlet 16 is formed in first portion 11a, while inlet 13 is formed in third portion 11c.

Figure 2:
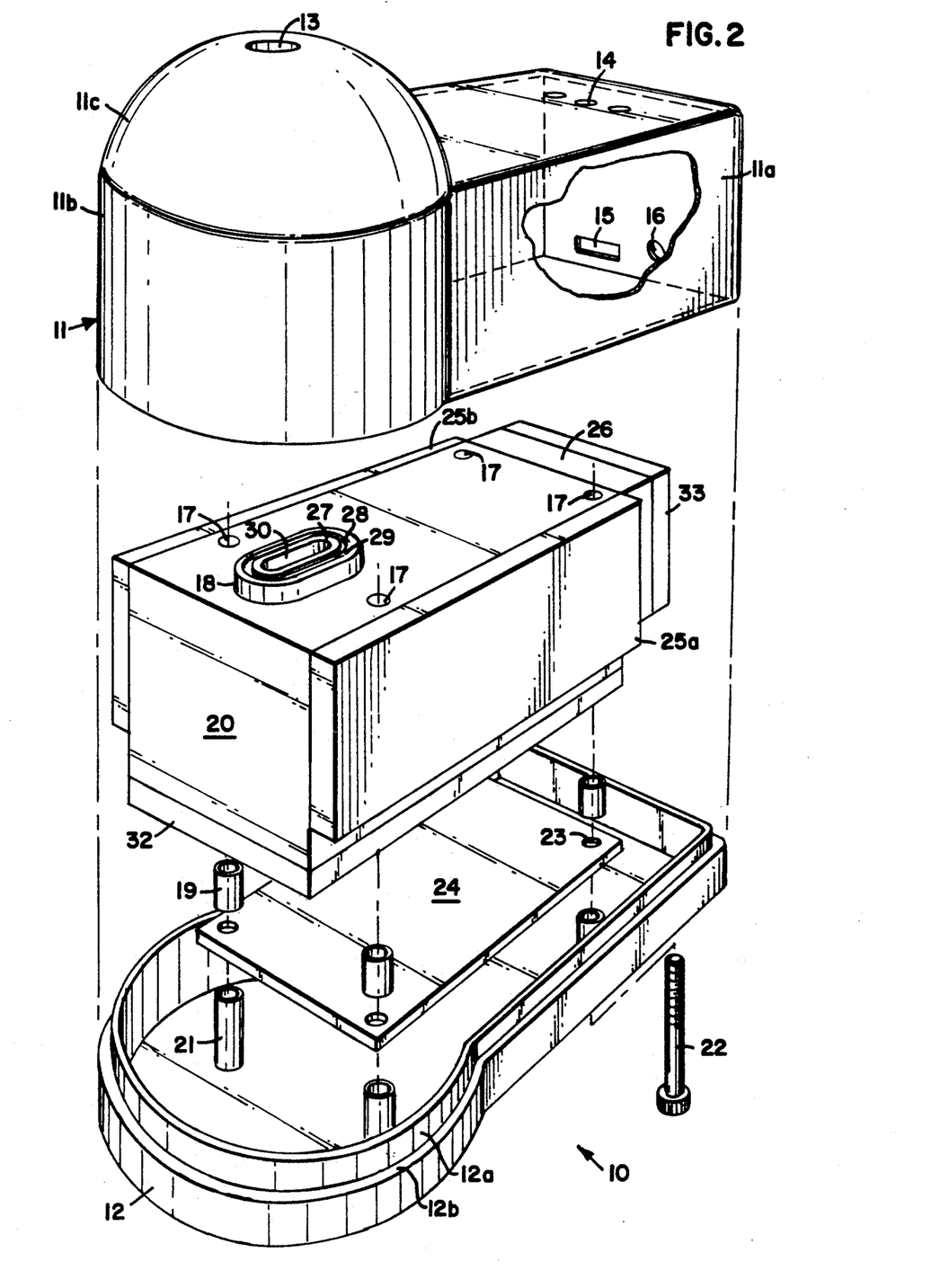
FIG. 2 is an exploded view of the apparatus of FIG. 1.

Referring next to FIG. 2, there is provided an exploded view of counter 10 with portions broken away. Detection chamber housing 20 resides within top 11 and bottom 12 of counter 10. Holes 17 formed through detection chamber housing 20 provide for bolts 22 to threadably secure the top 11 and bottom 12 covers together. The bolts 22 pass through bosses 21 and standoffs 19 to threadably engage appropriately so as to provide proper clearances to the various components of the counter 10. It will be apparent to those skilled in the art that although several bolts 22 are illustrated in the accompanying Figs., no effort has been made to correlate each and every bolt 22 to the holes 17, bosses 21 and stand-offs 19 illustrated. Those skilled in the art will recognize that other suitable fastening devices, welds, rivets, etc., might similarly be used in such a counter 10 as described herein.

Preferably top 11 and bottom 12 portions are constructed of investment cast stainless steel. However, those skilled in the art will realize that other materials such as aluminum might be used. The considerations for such materials being that the material's characteristics are suitable for materials it will come into contact with, among others.

Still referring to FIG. 2, cooperatively attached to detector housing 20 is first printed circuit board 32, first and second detectors 25a, 25b and laser housing 26. Second printed circuit board 33 is attached to a side of laser housing 26. On the top of detection chamber 20 is a cooperatively formed oval shaped connecting device 18, the oval shape being of the rounded corner rectangular type. The functionality of connecting device 18 is to place a curve in the inlet flow path which blocks out ambient room light, yet allows the particle flow to pass through unimpaired. Connecting device 18 provides for a raised lip portion 28, a lowered shoulder portion 29, and a raised shoulder portion 27. Lip and shoulder portions 27-29 mate with an oppositely disposed mating section (best seen in FIG. 3) located within top cover 11 so as to provide a liquid-tight seal when the various portions of counter 10 are secured together. Preferably, an O-ring 39 resides within lowered shoulder portion 28. Air inlet 30 is formed through connecting device 18.

Figure 3:
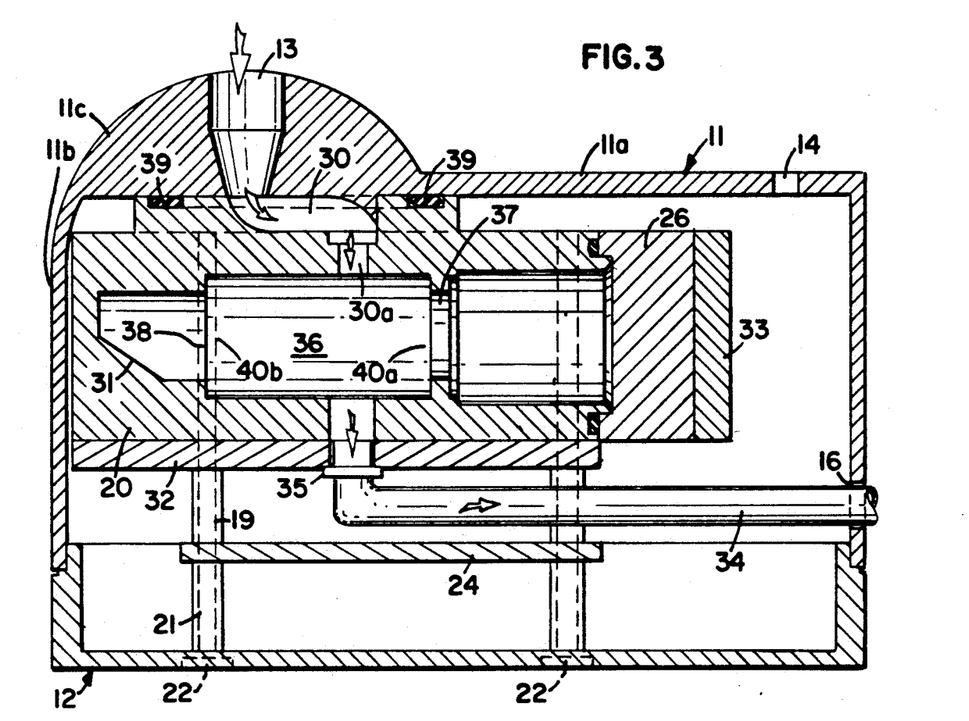
FIG. 3 is a cross section view of the apparatus of FIG. 1 taken through line 3—3 of FIG. 1.

Referring next to FIG. 3, the sample fluid enters the inlet nozzle 30 into a detector/laser chamber 36 formed within detection chamber housing 20. The inlet 30 bends ninety degrees (90°) twice to eliminate exterior ambient light from entering the counter 10.

Preferably, detection chamber housing 20 is plastic injection molded, although other materials might be used. The design considerations for detection chamber housing 20 will be described next.

The detector chamber 36 is preferably made from a block of electrically conductive, material. The conductive material is used to limit the build-up of static charges. The interior is painted with a black, highly absorbing paint for the wavelength of the laser 50 (described below) and is utilized to reduce laser background light.

Preferably detection chamber 36 has an inlet 30 at the top of the chamber 36, an exit 35 at the bottom of the chamber 36, and entrance aperture 37 for the collimated/focussed beam to enter the chamber 36 at a first end 40a and an exit 38 for the collimated/focused beam to exit the chamber 36 at a second end 40b. Additionally, chamber 36 has two holes formed through the sides of detection chamber housing 20 to provide for detectors 25 to reside proximate the sensing volume 63.

As used herein, the terms top, bottom, sides, and ends refer to the orientation of the detection chamber 36 as illustrated in FIG. 3. Those skilled in the art will appreciate that the actual location of the various components may be changed while still practicing the principles of the present invention.

Once the sample fluid enters the fluid flow path, it passes through, or intersects, a laser beam 60 (best seen in FIG. 4a) and between the two detector means 25a, 25b. The flow path is chosen to create the maximum amount of scattered light for the detector means 25. The use of two detectors 25 doubles the amount of light collected. Further, since the incident light signal is coherent, the noise level is raised only by a factor of the square root of 2 (i.e., the noise is incoherent), thereby producing a system with an improvement in signal to noise by the square root of two. To enhance this gain further, each detector may be constructed as a detector array. If a detector array of five (5) or more detectors are utilized, then signal to noise gain may be further enhanced. However, those skilled in the art will recognize that a single detector 25 might be utilized.

After intersecting the laser beam 60, the fluid continues through exit 35, tube 34 and finally exits counter 10 through exhaust port 16. Any number of well known vacuum creating devices may be utilized to draw the fluid sample through counter 10. An example of a suitable pump includes, but is not limited to a gas pump with critical orifice to control the volumetric flow or an internal dc brushless motor driving a vane pump with mass flow control. Tube 34 may be constructed of Tygon ® tubing or any other plastic tubing which tends to resist kinking and cracking.

Laser housing 26 houses laser diode 50, aperture 51, and focussing/collimating lens 54 (best seen in FIG. 4a). These three components together comprise a light source means. Preferably, a laser diode is utilized which provides short wavelength, high power, low noise and long life. In the preferred embodiment, the laser diode is a ML 4402; A manufactured by Mitsubishi, of Japan. The lens 54 is preferably a biaspheric collimating type lens. The lens 54 used in the preferred embodiment is a DOET45 manufactured by DO Industries of Rochester, N.Y. As noted above, a design consideration of the counter 10 is the use of a lens which has a given acceptance angle so as to minimize stray light from the back lasing facet into the detection chamber 36.

Aperture 51 is arranged and configured such that it is proximate the laser 50 and allows the beam 60 to pass through the aperture 51 to strike the collimating lens 54 within its acceptance angle. Preferably, the aperture 51 is placed approximately zero millimeters in front of the lasing facet (or as close as possible) and the aperture is approximately 0.063 inches in diameter. The beam 60 is then collimated/focussed by the collimating lens 54 and passes through a second and third aperture 52, 53 respectively and into the detection chamber 36. These apertures 56, 53 further reduce stray light. The second aperture 52 is placed approximately 0.25 inches from collimating lens 54 while the third aperture 53 is placed approximately 0.677 inches from second aperture 52. Each of the apertures 52, 53 are approximately 0.140 inches in diameter. The beam 60 then travels through detection chamber 36, forms a sensing volume 63 at the intersection of the fluid and the beam, and continues into beam stop means 31. Preferably, beam stop means 31 is a portion of the detection chamber housing 20 utilized at the Brewster angle for the wavelength and polarization of light utilized.

Counter 10 also includes a microprocessor and communications board 24, a laser drive printed circuit board 32, laser board 33 and a detector-amplifier board(s) 5a and 25b.

Figure 4B:
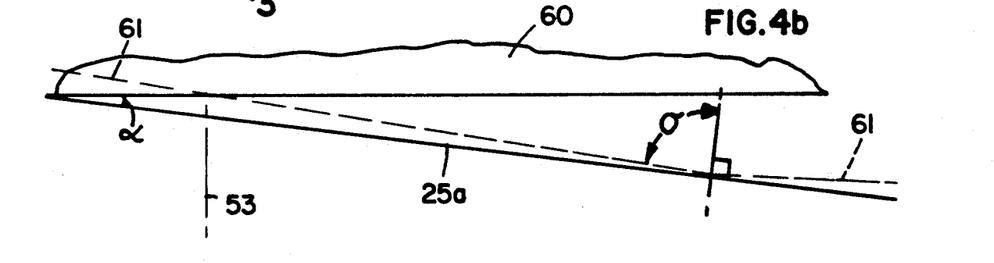

Referring next to FIGS. 4a and 4b, there is illustrated the arrangement and configuration of the detectors 25 in relation to the beam 60, stray light 61, and scattered light 62. As noted above, the detectors 25 are placed at an angle with respect to the x-z plane (the x-z plane goes into the page), wherein each of the detection surfaces of detectors 25 generally forms a mean plane (the mean plane is indicated by line in FIG. 4a, i.e., the mean plane goes into the page). This mean plane and the x-z plane determine an angle $\alpha$ between them. This angle $\alpha$ is determined so as to ensure that stray light (represented in FIGS. 4a and 4b by dotted line 61) when striking detector 25, strikes the detector 25 at an angle $\alpha$, wherein $\alpha$ is greater than the acceptance angle of the detector 25. Conversely, the angle $\alpha$ must be arranged such that angles $\beta(1)$ and $\beta(2)$ are within the acceptance range for the detectors 25. In the preferred embodiment, the detectors 25 create an angle $\alpha$ with respect to the x-z plane which is approximately eight degrees (8°). The acceptance angle for the detectors 25 is approximately 80°, such that $\beta(1)$ and $\beta(2)$ should be less than 80°.

In the preferred embodiment, the detectors 25 used are large area silicon chip PIN photodetectors. The detectors 25 have a low dark current or high resistivity. Also, preferably bare silicon is used (rather than the typical epoxy coating) due to its high index of refraction. This provides for better reflection of stray light at incident angles greater than the acceptance angle. An example of a manufacturer of the preferred detectors 25 is United Detector of Los Angeles, Calif. The detectors 25 have a mean surface which is approximately 10 mm by 20 mm and are spatially oriented such that the sensing volume is positioned slightly off center from the detectors 25. The exact position may be optimized by utilizing Mie theory.

Figure 5:
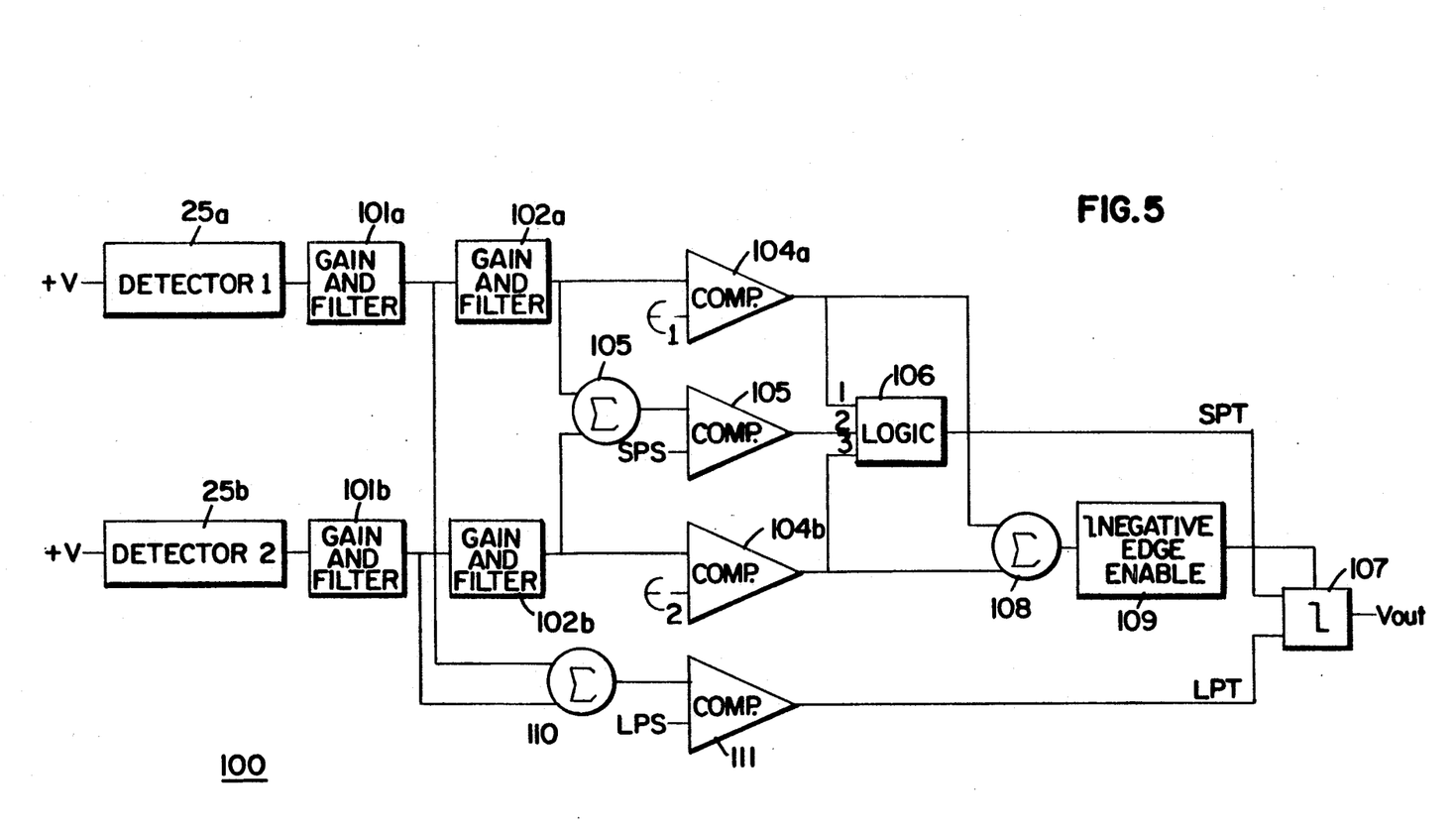
FIG. 5 is a functional block diagram of the coincidence detection means of counter 10 of FIG. 1.

Turning next to FIG. 5, there is illustrated a functional block diagram of a preferred embodiment which practices the coincidence detection means 100 of the present invention. Coincidence detection means 100 is part of amplifier coincidence block 150 in FIG. 6 below. The coincidence detection is preferably utilized by the logic illustrated in FIG. 5, although other ways of implementation will be evident to those skilled in the art, including software driven algorithms.

The first detector 25a of detection means 100 is connected to gain and filter 101a. Gain and filter 101a is then in turn connected to gain and filter 102a and to summing device 110. The second detector 25b is connected to gain and filter 101b, which is turn connected to gain and filter 102b and summing device 120. The outputs of gain and filter devices 102a, 102b are connected to comparators 104a and 104b respectively, while also connected to summing counter 103. The output of summing device 103 is provided to comparator 105. Also provided in an input to comparator 104a is Epsilon 1 ($\epsilon$1), while providing input to comparator 104b as Epsilon 2 ($\epsilon$2).

Two "size" channels are provided. The first channel is for particles greater or equal to 0.3 $\mu$m and the second is for particles greater or equal to 0.5 $\mu$m.

Providing input to comparator 105 is small particle sum ("SPS"). The output of comparators 104 and 105 are provided to logic block 106. Logic block 106 provides a small particle trigger pulse ("SPT") to block 107. Comparators 104a, 104b also provide output to summing device 108, the output of which enters negative edge enable block 109. The output of negative edge enable block is connected to output control block 107.

Gain and filters 101a, 101b also provide a signal to summing device 110 as noted above. Summing device 110 provides a signal to comparator 111. Large particle sum ("LPS") also provides input to comparator 111. The output signal of comparator 111 is utilized as a large particle trigger ("LPT") pulse to block 107. In operation, when a positive pulse simultaneously strikes both detectors 25, the detectors 25 each provide an output pulse responsive to the amount of light incident, or striking, the detector 25. The output pulse from the detectors 25 are provided to gain and filter blocks 101a and 101b respectively. In the event that the pulse is large (i.e., a large particle on the order of magnitude of 0.50 μm) then summing device 110 provides a large enough signal to activate comparator 111. Signals also pass through gain and filters 102a, 102b, summed at summing device 103 and provided to comparators 104a, 104b. The signal output from summing device 103 activates comparator 105, with respect to SPS, then logic block 106, by ensuring that all three outputs of comparators 104a, 104b and 105 are each high (i.e., signals present), provides a signal SPT to output control block 107. If either of the inputs 102 of the logic block 10b are not high within a certain period of time of each other, then the event is qualified as a non-particle event.

Those skilled in the art will recognize that either positive or negative logic might be used and that various signal comparators might also be used. Further, the magnitude of SPS and LPS might be adjusted. The coincidence determining means 100 are designed in large part to qualify events so as to eliminate false signals from various noise sources/incidents. Such false signals typically occur at a low rate with varying amplitude. Those skilled in the art will also realize that the triggering of an LPT signal causes a qualification of the signal by logic block 106, while a large particle count is eventually counted (if the event is qualified as an actual particle) at block 107. Negative edge enable block 109 may also provide a reset function for block 107 at the end of an event. Summing device 108 is also provided with the signals from comparators 104a, 104b which provides a negative edge enable to block 107 in order to provide a voltage output signal of different time basis for signals SPT or LPT.

The output signal, SPT or LPT, for a qualified event is provided to a microprocessor 151 which preferably correlates the time versus concentration of detected particles for user reference. This data is preferably accumulated for two different particle size ranges, as described above, with one data set being provided for each particle size.

Figure 6:
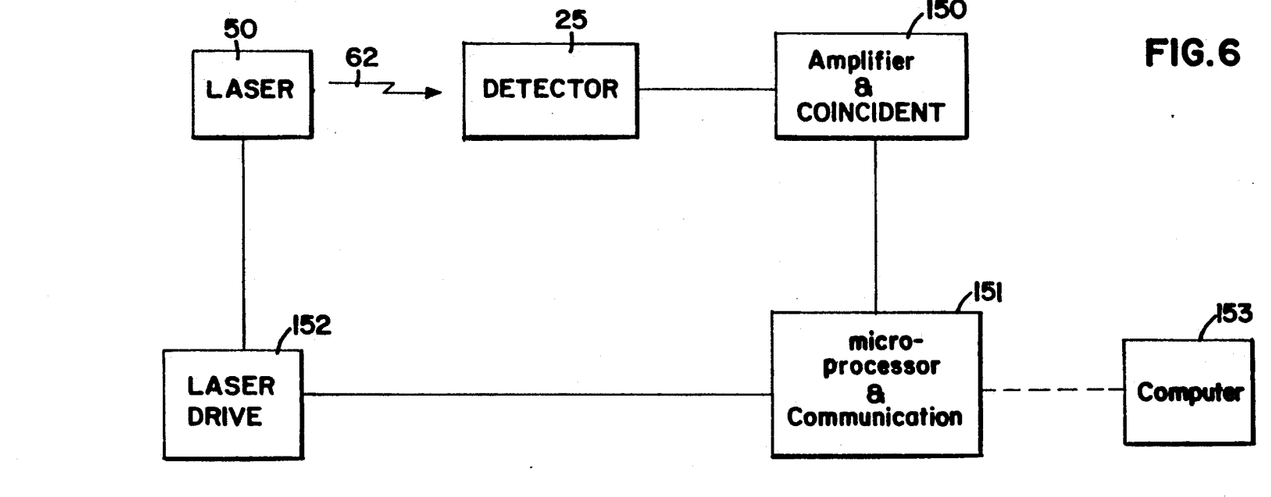
FIG. 6 is a functional block diagram of the electrical sections of counter 10 of FIG. 1.

Next, turning to FIG. 6, there is illustrated a block diagram of the functional electrical elements of a preferred embodiment of the present invention. Scattered light 62 from laser 50 (i.e., light scattered from beam 60), strikes detectors 25 which detects the light and generates a signal. The signal is transmitted to amplifier and coincident circuit detection block 150. The signal is amplified and coincident signals are detected as described above. Validated signals are thereafter transmitted to microprocessor and communication block 151. Here, fluctuations in the laser output power are compared to the signals received from amplifier and coincident block 150. Laser drive 152 provides power to the laser 50. Microprocessor and communications block 151 is also connected to the LED's 14 and is connected via an appropriate connector device (not shown) through port 15 (best seen in FIG. 2) to a computer 153.

While not specifically detailed in FIGS. 5 and 6, it will be understood that all functional blocks, laser drive 152, and other electrical components are properly connected to appropriate bias and reference supplied so as to operate in their intended manner. Further, the laser drive 152 of counter 10 preferably provides constant power output to the laser 50.

It is to be understood that even though numerous characteristics and advantages of the present invention have been set forth in the foregoing description, together with details of the structure function of the invention, the disclosure is illustrative only and changes may be made in detail, especially in matters of the arrangement of the flow path through the counter and the supporting hardware and software routines including the use of positive or negative logic and comparisons, to the full extent indicated by the broad general meaning of the terms in which the appended claims are expressed.

We claim:

1. A continuous flow particle counter apparatus, of the type wherein a sample fluid is passed through a beam of light, wherein the intersection of the sample fluid flow and the beam of light define a sensing volume, and wherein particles suspended in the sample fluid scatter light, the particle counter comprising:
    (a) a light source means for generating the beam of light;
    (b) sensor means for directly collecting the scattered light and for generating signals responsive to the scattered light and wherein asid sensor means are arranged and configured to reflect stray light from the vicinity of said light source means and absorb the scattered light from particles intersecting the sensing volume, said sensor means being oriented at an oblique angle with respect to the beam of light, whereby reimaging optics are not required.

2. The apparatus of claim 1, wherein said sensor means include a light sensitive surface, generally defining a mean plane, and said sensor means have an acceptance angle, wherein said acceptable angle is defined as an angle relative to the normal to said mean plane whereby light incident on said sensor means at an angle larger than said acceptance angle is reflected and light incident on said sensor means at an angle smaller than said acceptance angle is absorbed, and wherein said mean plane is aligned at an angle α with respect to a plane formed by the beam of light and the sample fluid flow, wherein α is determined by the compliment of said acceptance angle of said light sensitive surface.

3. The apparatus of claim 2, wherein α equals an angle between 2 degrees and 25 degrees.

4. The apparatus of claim 2, wherein α equals an angle of 8 degrees.

5. The apparatus of claim 1, wherein said sensor is comprised of at least two sensor devices, and further comprising a coincidence detection means, cooperatively attached to said sensors, for rejecting signals which are not created by scattered light.

6. The apparatus as recited in claim 1, further including vacuum means in fluid communication with the fluid sample for drawing the fluid sample through the sensing volume.

7. The apparatus as recited in claim 1, further including a microprocessor for determining the number of particles per unit volume of the sample fluid.

8. The apparatus of claim 1, further including a light stop for blocking the beam of light.

9. The apparatus of claim 8, wherein said beam of light has a wavelength and said light stop includes a Brewster angle for said wavelength of the beam of light.

10. The apparatus of claim 1, wherein said beam of light is generally collimated and forms a straight path, and further comprising a plate having an aperture formed there through, asid plate being spatially oriented within said path of the beam of light, wherein the beam of light passes through said aperture and wherein light which diverges from said path or which does not emanate from said source tends to be blocked by said plate.

11. A particle counter apparatus, of the type wherein particles suspended in a sample fluid flow scatter light, the apparatus comprising:
   (a) a source of light;
   (b) a lens, said lens arranged and configured to focus light from said source into a beam, said beam intersecting the fluid flow wherein a sensing volume is formed; and
   (c) one or more oppositely disposed large area photodetectors arranged and configured such that said beam operatively passes said photodetector without being operatively incident, said photodetector including a light sensitive surface generally defining a mean plane, said photodetector oriented wherein said mean plane is spatially oriented at an oblique angle to the plane defined by said beam and the fluid flow and located proximate said sensing volume, whereby said photodetector directly collects the scattered light without requiring reimaging optics in order to detect particles in the sample fluid and wherein said angle is determined in part by the acceptance angle of said large area photodetectors.

12. The apparatus of claim 11, further comprising a light block including a Brewster angle, said light block arranged and configured such that said beam is operatively incident on said light block, whereby the light which is not scattered by the particles is absorbed by said light block.

13. The apparatus of claim 11, wherein said lens has an acceptance angle, and further comprising an aperture surface, said aperture surface arranged and configured spatially between said light source and said lens, said aperture surface having a first hole formed therethrough, said hole configured in accordance with the acceptance angle of said lens, wherein light not within the acceptance angle of said lens is blocked by said aperture surface.

14. The apparatus of claim 13, further comprising a second aperture plate, said second aperture plate arranged and configured spatially between said collimating lens and the sensing volume, said second aperture plate having a second hole formed therethrough for said beam to pass through, whereby light not within said beam is eliminated.

15. The apparatus of claim 11, wherein there are at least two oppositely disposed large area photodetectors, and further comprising coincidence determining means, cooperatively connected to said photodetectors, for comparing signals generated by said photodetectors wherein only events which trigger a plurality of said detectors are counted.

16. The apparatus of claim 15, wherein each of said photodetectors includes an array of photodetectors.

17. A particle detector apparatus, of the type wherein a sensing volume is defined by the intersection of a sample fluid and a beam of light generated by a light source, the sample fluid containing particulate matter and the beam having a longitudinal axis, the particles scattering light from the beam when the particles intersect the sensing volume, the apparatus comprising: detector means, arranged and configured proximate the beam thereby allowing the beam to operatively pass between said detector means, for detecting light scattered from the beam by particles intersecting the sensing volume, where in said detector means include at least one light sensitive surface generally defining a mean plane and wherein said light sensitive surface reflects light which strikes said light sensitive surface at an angle greater than a predetermined angle with respect to the normal to said mean plane, said detector means being further arranged and configured with respect to the longitudinal axis of the beam wherein said mean plane forms an angle with the longitudinal axis of the beam of greater than zero degrees and less than 90 degrees such that stray light is reflected off of said detector means and light scattered by particles is detected by said detector means, whereby the need for reimaging optics is eliminated and stray light from the light source is rejected.

18. A method for detecting particles in a sample fluid utilizing light scattering techniques without requiring reimaging optics, the method comprising the steps of:
   (a) generating a beam of light;
   (b) directing said beam between photosensitive surfaces, said surfaces having an acceptance angle, said surfaces aligned at oblique angles with respect to the longitudinal axis of said beam wherein light diverging from said beam strikes said surfaces at an angle greater than the acceptance angle of said photosensitive surfaces;
   (c) directing the sample fluid through said beam of light proximate said photo sensitive surfaces, wherein a sensing volume is formed at the intersection of said beam and the sample fluid, whereby particles in the sample fluid scatter light out of said beam; and
   (d) collecting and detecting concomitant light, scattered from said beam by particles, incident on said photosensitive surfaces.

19. The method of claim 18, wherein said beam of light includes a wavelength and further comprising the steps of blocking said beam of light with a light stop having a Brewster angle for the wavelength of said beam of light.

20. The method of claim 18, further comprising the steps of comparing detected light from said photosensitive surfaces wherein only detected light which is detected by more than one of said light sensitive surfaces is counted as a particle.

* * * * *